United States Patent
Prakash et al.

(10) Patent No.: US 6,291,004 B1
(45) Date of Patent: Sep. 18, 2001

(54) BASIC SALTS OF N-[N-(3,3-DIMETHYLBUTYL)-L-α-ASPARTYL]-L-PHENYLALANINE 1-METHYL ESTER

(75) Inventors: Indra Prakash, Hoffman Estates; Kurt L. Wachholder, Elgin, both of IL (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 09/146,963

(22) Filed: Sep. 4, 1998

Related U.S. Application Data

(60) Provisional application No. 60/058,506, filed on Sep. 11, 1997.

(51) Int. Cl.$^7$ .................................................. A23L 1/236
(52) U.S. Cl. ................................ 426/548; 560/40; 560/41
(58) Field of Search ............................... 426/548; 560/40, 560/41

(56) References Cited

U.S. PATENT DOCUMENTS

| | | | |
|---|---|---|---|
| 4,031,258 | 6/1977 | Haas et al. | 426/548 |
| 4,153,737 | 5/1979 | Berg et al. | 426/548 |
| 5,480,668 | 1/1996 | Nofre et al. | 426/548 |
| 5,510,508 | 4/1996 | Claude et al. | 560/41 |
| 5,728,862 | 3/1998 | Prakash | 560/40 |

FOREIGN PATENT DOCUMENTS

07680141A1    4/1997    (EP).

OTHER PUBLICATIONS

Goodman et al., X–Ray Structures of New Dipeptide Taste Ligands, J. Peptide Sci., 4, 229–238, 1998.*

Benedetti, E. et al., "The Structure of New Dipeptide Taste Ligands", American Peptide Symposium, Nashville, TX, (Jun. 1997) P233 p 2–127.

Database WPI, Week 44, Derwent Publications Ltd., XP002089909 "Sweetening salts–preparation by reaction of acid sweeteners with dipeptide derivative of 1–aspartic acid" (1986).

J. Pept. Sci., vol. 4, No. 4 Apr. 1998, pp. 229–238, XP002089908 M. Goodman et al. "X–ray structures of new dipeptide taste ligands".

* cited by examiner

*Primary Examiner*—Leslie Wong
(74) *Attorney, Agent, or Firm*—Fitzpatrick, Cella, Harper & Scinto

(57) ABSTRACT

Dipeptide sweeteners are disclosed that are basic salts of N-[N-(3,3-dimethylbutyl)-L-α-aspartyl]-L-phenylalanine 1-methyl ester represented by the formula

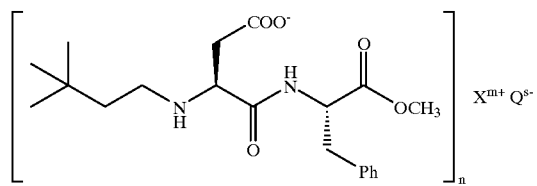

wherein $X^{m+}$ is selected from the group consisting of $Na^+$, $K^+$, $Al^{3+}$, $Fe^{2+}$, $Fe^{3+}$, $Ca^{2+}$, $Mg^{2+}$, $NH_4^+$ and $Zn^{2+}$; $Q^{s-}$ absent or a physiologically acceptable counter anion; and m–s=n. Also disclosed is a liquid low-calorie sweetener containing such basic salts.

11 Claims, 1 Drawing Sheet

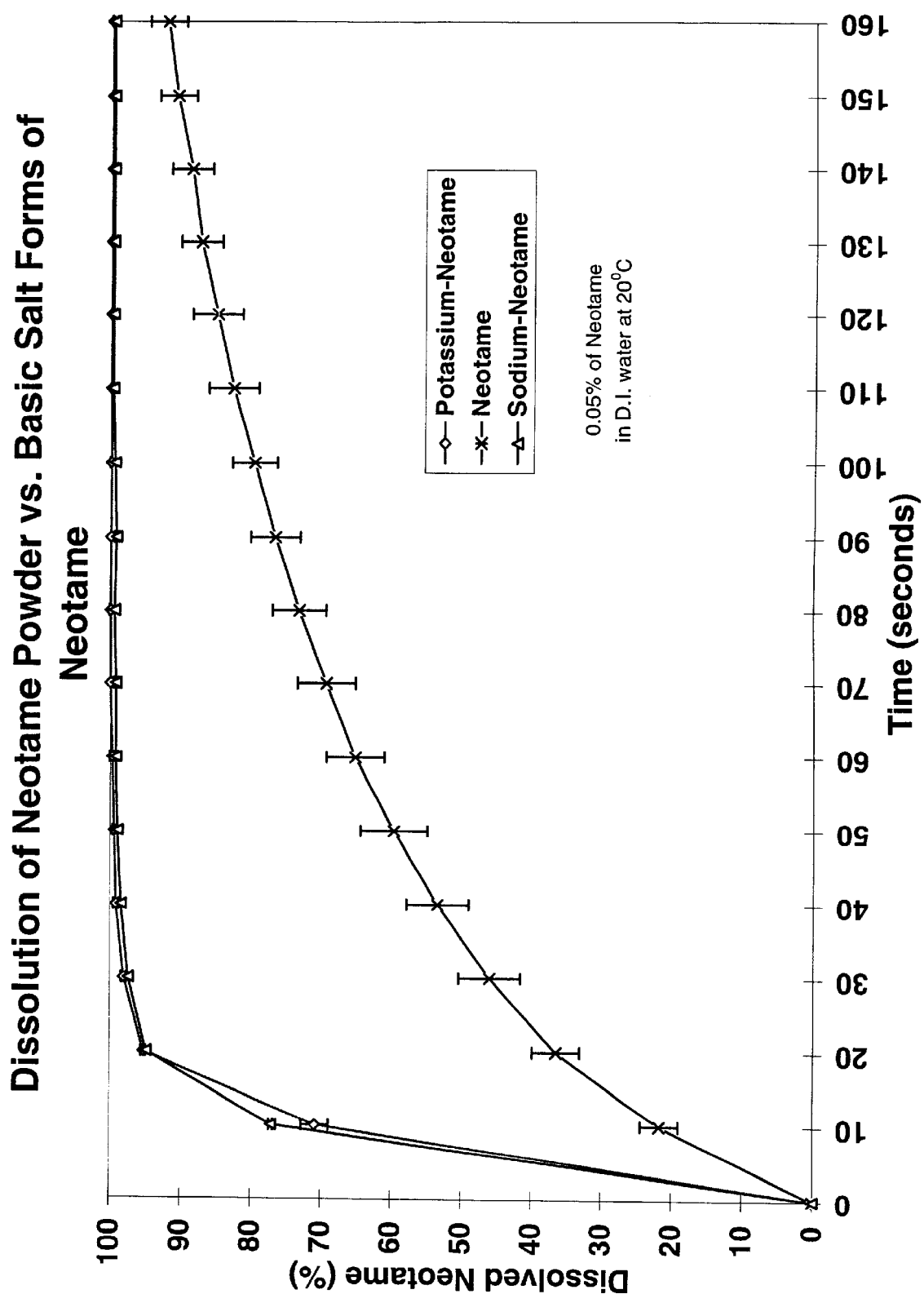

BASIC SALTS OF N-[ N-(3,3-DIMETHYLBUTYL)-L-α-ASPARTYL]-L-PHENYLALANINE 1-METHYL ESTER

This invention claims the benefit of U.S. Provisional Application No. 60/058,506, filed Sep. 11, 1997.

BACKGROUND OF THE INVENTION

1. Field of the Invention

This invention relates to novel sweeteners. In particular, the invention relates to basic salts of the N-alkylated aspartame derivative, N-[N-(3,3-dimethylbutyl)-L-α-aspartyl]-L-phenylalanine 1-methyl ester, i.e., neotame. The invention also relates to a liquid low calorie sweetener containing such basic salts.

2. Related Background Art

It is known that various N-substituted derivatives of aspartame, such as disclosed in U.S. Pat. No. 5,480,668, are useful as sweetening agents. In particular, the N-alkylated aspartame derivative, N-[N-(3,3-dimethylbutyl)-L-α-aspartyl]-L-phenylalanine 1-methyl ester, is known as an extremely potent sweetening agent since its sweetening potency, on a weight basis, has been reported to be at least 50 times that of aspartame and about 10,000 times that of sucrose.

Since sweetening agents are often employed in aqueous solutions and beverages, it is important that they have an acceptable dissolution rate and an effective level of solubility to be commercially practicable. U.S. Pat. No. 4,031,258 describes certain inorganic salts of dipeptide sweeteners that provide improved dissolution and solubility. N-[N-(3,3-dimethylbutyl)-L-α-aspartyl]-L-phenylalanine 1-methyl ester, however, is not disclosed or suggested.

It is known that the physical properties, as well as the stability of aspartame and other peptides can be modified by conversion to their salts. This is disclosed, for example, in U.S. Pat. Nos. 4,031,258 and 4,153,737. U.S. Pat. No. 4,153,737 also describes concentrated liquid low calorie sweetener.

Structurally, however, N-[N-(3,3-dimethylbutyl)-L-α-aspartyl]-L-phenylalanine 1-methyl ester and aspartame differ in that, in N-[N-(3,3-dimethylbutyl)-L-α-aspartyl]-L-phenylalanine 1-methyl ester, a bulky neohexyl substituent is present on the amine nitrogen.

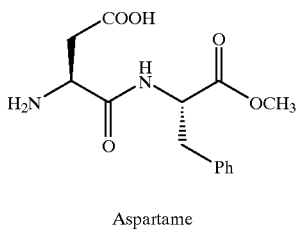

Aspartame

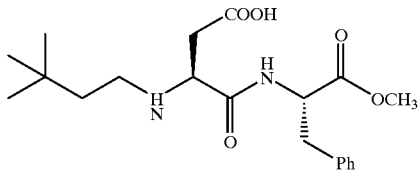

Neotame

This structural difference results in dramatic differences in the physical and chemical properties of these compounds. For example, the melting point of N-[N-(3,3-dimethylbutyl)-L-α-aspartyl]-L-phenylalanine 1-methyl ester is 80° C., while that of aspartame is 248° C. In addition, N-[N-(3,3-dimethylbutyl)-L-α-aspartyl]-L-phenylalanine 1-methyl ester has much higher solubility in organic solvents than aspartame, and a much lower solubility in water. It is also known that N-[N-(3,3-dimethylbutyl)-L-α-aspartyl]-L-phenylalanine 1-methyl ester has a higher stability than aspartame under some pH conditions, as described in U.S. Pat. No. 5,480,688. The pronounced difference in sweetness between the two compounds is further evidence of their chemical dissimilarity.

Moreover, it is also known that a primary amino group such as the one on aspartame (pKa 7.7) generally has a different pKa than those from a secondary amino group such as the one on N-[N-(3,3-dimethylbutyl)-L-α-aspartyl]-L-phenylalanine 1-methyl ester (pKa 8.1). Moreover, the pKa's of an amino acid are known to have a profound impact on food applications (Labuza, T. P. and Basisier, M. W., 1992, "Physical Chemistry of Foods", H. G. Schwartzber and R. W. Hartel (Eds.), Marcel Dekker, Inc., New York). It is also well known that a secondary amine group can not form Schiff base type compounds with carbonyl compounds while a primary amine may. Furthermore, N-[N-(3,3-dimethylbutyl)-L-α-aspartyl]-L-phenylalanine 1-methyl ester exhibits physiologically different behavior than aspartame as exemplified by the dramatic difference in sweetness. These differences are clearly indicative that the characteristics and properties of one can not be said to suggest those of the other.

While N-[N-(3,3-dimethylbutyl)-L-α-aspartyl]-L-phenylalanine 1-methyl ester is a highly potent sweetener, it is sparingly soluble in water and can give rise to dusting problems. Therefore, there is a need for N-[N-(3,3-dimethylbutyl)-L-α-aspartyl]-L-phenylalanine 1-methyl ester derivatives that have good dissolution and solubility properties in aqueous systems, and avoid dusting problems often encountered with fine powders.

SUMMARY OF THE INVENTION

This invention relates to dipeptide sweeteners that are basic salts of N-[N-(3,3-dimethylbutyl)-L-α-aspartyl]-L-phenylalanine 1-methyl ester possessing good dissolution and solubility properties in aqueous systems. In particular, the basic salts of N-[N-(3,3-dimethylbutyl)-L-α-aspartyl]-L-phenylalanine 1-methyl ester of this invention are represented by the formula.

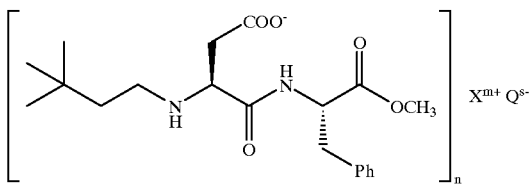

wherein $X^{m+}$ is selected from the group consisting of $Na^+$, $K^+$, $Al^{3+}$, $Fe^{2+}$, $Fe^{3+}$, $Ca^{2+}$, $Mg^{2+}$, $NH_4^+$ and $Zn^{2+}$, $Q^{s-}$ is absent or a physiologically acceptable counter anion, and m−s=n (when Q is absent s is zero). Preferably n is 1, 2 or 3. The invention is also related to a liquid low calorie sweetener containing the basic salts of this invention.

BRIEF DESCRIPTION OF THE DRAWING

The FIGURE is a graph comparing the aqueous dissolution of N-[N-(3,3-dimethylbutyl)-L-α-aspartyl]-L-phenylalanine 1-methyl ester at a target concentration of 0.05% by weight with equivalent neotame concentrations, i.e. the concentration of the neotame delivered in each case is the same, of the sodium and potassium salts of N-[N-(3,3-dimethylbutyl)-L-α-aspartyl]-L-phenylalanine 1-methyl ester.

DETAILED DESCRIPTION OF THE INVENTION

This invention is directed to basic salts of N-[N-(3,3-dimethylbutyl)-L-α-aspartyl]-L-phenylalanine 1-methyl ester, i.e., basic salts of neotame. U.S. Pat. No. 5,480,668, U.S. Pat. No. 5,510,508 and U.S. Pat. No. 5,728,862, which describe the preparation of N-[N-(3,3-dimethylbutyl)-L-α-aspartyl]-L-phenylalanine 1-methyl ester are incorporated by reference herein as if fully set forth. Thus, the starting material may be readily prepared by one of ordinary skill in the art without undue experimentation.

The basic salts of this invention may be prepared by adding N-[N-(3,3-dimethylbutyl)-L-α-aspartyl]-L-phenylalanine 1-methyl ester to a solvent or a mixture of solvents. Exemplary solvents may include water, acetone, methanol, ethanol, acetonitrile, tetrahydrofuran and the like. N-[N-(3,3-dimethylbutyl)-L-α-aspartyl]-L-phenylalanine 1-methyl ester need not be completely soluble in the solvent. Thereafter, an equivalent amount of base is added to the solution and stirred for a period of time to achieve formation of the basic salt. It will be obvious to one skilled in the art that the order of addition of N-[N-(3,3-dimethylbutyl)-L-α-aspartyl]-L-phenylalanine 1-methyl ester and the base may not be critical. The salt may be recovered by freeze drying or spray drying the resulting solution. Basic salts of N-[N-(3,3-dimethylbutyl)-L-α-aspartyl]-L-phenylalanine 1-methyl ester prepared under these conditions do not show any racemization. However, addition of excess of base (more than 1 equivalent) does cause hydrolysis/racemization.

The bases employed in the preparation of the basic salts of this invention are typically selected from compounds that have a pKa effectively higher than the pKa of N-[N-(3,3-dimethylbutyl)-L-α-aspartyl]-L-phenylalanine 1-methyl ester to result in the formation of the desired salt. Such compounds include, for example, sodium bicarbonate, sodium carbonate, sodium hydroxide, potassium bicarbonate, potassium carbonate, potassium hydroxide, magnesium hydroxide, aluminum hydroxide, calcium hydroxide, ferric oxide, ferrous oxide, ammonium hydroxide, ammonium acetate, ammonium carbonate, zinc carbonate or zinc hydroxide. As such, $X^{m+}$ is a physiologically acceptable cation selected from the group consisting of $Na^+$, $K^+$, $Al^{3+}$, $Fe^{2+}$, $Fe^{3+}$, $Ca^{2+}$, $Mg^{2+}$, $NH_4^+$ and $Zn^{2+}$. These ions can be used alone or in combination. The basic salts of this invention may also include a physiologically counter anion $Q^{s-}$. Such counter ions include, for example, $OH^-$, $(OH)_2^{2-}$, $CH_3CO_2^-$, $Cl^-$, $SO_4^{2-}$, $PO_4^{3-}$, $O^{2-}$ or $O_2^{4-}$.

Particularly preferred basic salts of this invention include the sodium, potassium, magnesium, aluminum, calcium, ferric, ferrous, ammonium hydroxide and zinc salts of N-[N-(3,3-dimethylbutyl)-1-L-α-aspartyl]-L-phenylalanine 1-methyl ester.

It is believed that the basic salts of this invention provide a number of improved properties over those of N-[N-(3,3-dimethylbutyl)-L-α-aspartyl]-L-phenylalanine 1-methyl ester. In particular, the aqueous solubility is increased and the dissolution rate of the composition is greatly improved. These basic salts of neotame are sweet in taste. Thus, the basic salts of N-[N-(3,3-dimethylbutyl)-L-α-aspartyl]-L-phenylalanine 1-methyl ester will be particularly useful in beverage systems, particularly since additional methods or mechanical preparations are diminished or not necessary to provide for quick dissolution such as desired in a table top sweetener. The basic salts of this invention may be admixed with known bulking agents to prepare tablets, powdered and granular sweeteners using methods well known to those skilled in the art. Another advantage of the basic salts of this invention is that they do not exhibit the dusting problems associated with N-[N-(3,3-dimethylbutyl)-L-α-aspartyl]-L-phenylalanine 1-methyl ester.

The basic salts may also be used to prepare a liquid, low-calorie sweetener by dissolving a high concentration of the basic salt of this invention in an aqueous or alcoholic system, e.g., water, propylene glycol, a water/propylene glycol mixture, ethanol or a water/ethanol mixture. Such a liquid, low-calorie sweetener may find utility in such foodstuffs as gelatin desserts, fruit flavored beverages, cereal, cake mixes, fruit juices, syrups, salad dressings, pet foods, carbonated soft drinks, table top sweeteners and the like. Such utilities are not restrictive since other applications may include cough medicines, tonics and the like. One embodiment of this invention of particular interest contemplates a liquid table top sweetener as a replacement for sucrose and other known sweeteners. The liquid low calorie sweetener generally will contain up to about 40% by weight of the basic salt of N-[N-(3,3-dimethylbutyl)-L-α-aspartyl]-L-phenylalanine 1-methyl ester, the concentration depending, of course, on the desired end use.

The Examples which follow are intended as an illustration of certain preferred embodiments of the invention, and no limitation of the invention is implied.

EXAMPLE 1

Sodium Salt of N-[N-(3,3-dimethylbutyl)-L-α-aspartyl]-L-phenylalanine 1-methyl ester Sodium bicarbonate (1.06 g, 0.0126 mol) was dissolved in 150 ml of water. N-[N-(3,3-dimethylbutyl)-L-α-aspartyl]-L- phenylalaninel-methyl ester (5.00 g, 0.0126 mol) was added and the slurry was stirred for 24 hours. The resulting clear solution was then freeze dried to yield 5.2 g of a white solid. The resulting sodium salt dissolved in water (0.1 g in 100 mL) almost instantly by visual observation and in less than 110 seconds by spectrophotometric analysis. Anal. Calcd for $C_{20}H_{29}N_2O_5Na\cdot H_2O$: C, 57.39; H, 7:48; N, 6.69. Found: C, 57.65; H, 7.44 ; N, 6.75.

EXAMPLE 2

Potassium Salt of N-[N-(3,3-dimethylbutyl)-L-α-aspartyl]-L-phenylalanine 1-methyl ester Potassium bicarbonate (0.51 g, 0.0050 mol) was dissolved in 50 ml of water. N-[N-(3,3-dimethylbutyl)-L-α- aspartyl]-L-phenylalanine 1-methyl ester (2.00 g, 0.0050 mol) was dissolved in acetone (50 mL) and added to the aqueous solution of potassium bicarbonate. The production of carbon dioxide gas was evident from the formation of bubbles on the walls of the flask. The solution was stirred for 1 hour and the organic solvent removed on a rotary evaporator. The resulting clear solution was freeze dried to yield 2.15 g of a white solid. The potassium salt dissolved in water (0.1 g in 100 mL) almost instantly by visual observation and in less than 60 seconds by spectrophotometric analysis. Anal. Calcd for $C_{20}H_{29}N_2O_5K\cdot H_2O$: C, 55.26; H, 7.20; N, 6.45. Found: C, 55.28; H, 7.29; N, 6.62.

EXAMPLE 3

Magnesium Salt of N-[N-(3,3-dimethylbutyl)-L-α-aspartyl]-L-phenylalanine 1-methyl ester Magnesium hydroxide (0.147 g, 0.0025 mol) was mixed with 300 mL of water and N-[N-(3,3-dimethylbutyl)-L-α-aspartyl]-L-phenylalanine 1-methyl ester (2.00 g, 0.0050 mol) was added and the slurry stirred. After stirring for 3 days the slurry became a clear solution. This aqueous solution was then freeze dried to yield 1.99 g of a fluffy white solid. The magnesium salt product dissolved in water (0.1 g in 100 mL) instantly (visual observation). Anal. Calcd for $C_{40}H_{58}N_4O_{10}Mg\cdot 5H_2O$: C, 55.25; H, 7.89; N, 6.45. Found: C, 55.07; H, 7.64; N, 6.68.

EXAMPLE 4

Aluminum Salt of N-[N-(3,3-dimethylbutyl)-L-α-aspartyl]-L-phenylalanine 1-methyl ester Aluminum hydroxide (0.161 g, 0.00168 mol) was mixed with water (300 mL). N-[N-(3,3-dimethylbutyl)-L-α-aspartyl]-L-phenylalanine 1-methyl ester (2.00 g, 0.0050 mol) was added and the mixture stirred for 3 days. Some solid material remained in the flask. This was removed by filtration and the clear filtrate was freeze dried to yield 2.01 g of a white solid. The aluminum salt dissolved in water (0.1 g in 100 mL) in 120 seconds (visual observation). Anal. Calcd for $C_{60}H_{87}N_6O_{15}Al\cdot 3H_2O$: C, 59.39; H, 7.74; N, 6.93. Found: C, 59.93; H, 8.02; N, 7.04.

EXAMPLE 5

Calcium Salt of N-[N-(3,3-dimethylbutyl)-L-α-aspartyl]-L-phenylalanine 1-methyl ester Calcium hydroxide (0.187 g, 0.0025 mol) was mixed with water (300 mL). N-[N-(3,3-dimethylbutyl)-L-α-aspartyl]-L-phenylalanine 1-methyl ester (2.00 g, 0.0050 mol) was added and the mixture was stirred for 3 days. The insoluble solid was removed by filtration and the clear filtrate was freeze dried to yield 1.21 g of a white solid. The resulting calcium salt dissolved in water (0.1 g in 100 mL) in approximately 5 minutes (visual observation). The calcium salt of N-[N-(3,3-dimethylbutyl)-L-α-aspartyl]-L-phenylalanine 1-methyl ester has high solubility in water, but it appears to form a supersaturated solution. Anal. Calcd for $C_{40}H_{58}N_4O_{10}Ca\cdot 3H_2O$: C, 56.58; H, 7.61; N, 6.83. Found: C, 56.61; H, 7.52; N, 6.93.

Comparative Example 1

Dissolution of N-[N-(3,3-dimethylbutyl)-L-α-aspartyl]-L-phenylalanine 1-methyl ester in Water N-[N-(3,3-dimethylbutyl)-L-α-aspartyl]-L-phenylalanine 1-methyl ester (0.05–0.1 g) was dissolved in water (100 mL). The compound completely dissolved in 5–7 minutes (visual observation). The dissolution of 1.0 g of N-[N-(3,3-dimethylbutyl)-L-α-aspartyl]-L-phenylalanine 1-methyl ester in 100 mL of water required approximately 45 minutes.

Other variations and modifications of this invention will be obvious to those skilled in this art. This invention is not to be limited except as set forth in the following claims.

What is claimed is:

1. A basic salt of N-[N-(3,3-dimethylbutyl)-L-α-aspartyl]-L-phenylalanine 1-methyl ester represented by the formula

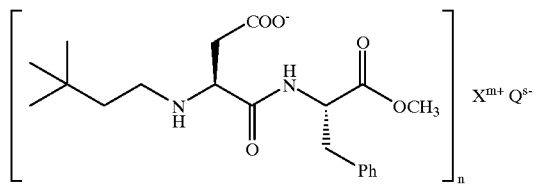

wherein $X^{m+}$ is selected from the group consisting of $Na^+$, $K^+$, $Al^{3+}$, $Fe^{2+}$, $Fe^{3+}$, $Ca^{2+}$, $Mg^{2+}$, $NH_4^+$ and $Zn^{2+}$; $Q^{s-}$ is absent or a physiologically acceptable counter anion; and m−s=n wherein the basic salt is sweet in taste.

2. A basic salt according to claim 1, wherein n is 1, 2 or 3.

3. A basic salt according to claim 2, wherein $Q^{s-}$ is selected from the group consisting of $OH^-$, $(OH)_2^{2-}$, $CH_3CO_2^-$, $Cl^-$, $SO_4^{2-}$, $PO_4^{3-}$, $O^{2-}$ or $O_2^{4-}$.

4. A basic salt according the claim 3, wherein $X^{m+}Q^{s-}$ is selected from the group consisting of $Mg(OH)^+$, $Al(OH)_2^+$ and $Ca(OH)^+$ and n is 1.

5. A basic salt according to claim 3, wherein $X^{m+}Q^{s-}$ is selected from the group consisting of $Fe_2O_2^{2+}$ or $Fe^{2+}$ and n is 2.

6. A basic salt according to claim 1, wherein $Q^{s-}$ is absent, n is 1 and $X^{m+}$ is selected from the $Na^+$, $K^+$ or $NH_4^+$.

7. A liquid low-calorie sweetener composition comprising a basic salt of a dipeptide-sweetener represented by the formula

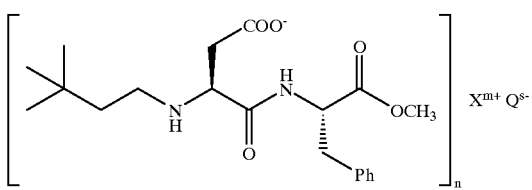

wherein $X^{m+}$ is selected from the group consisting of $Na^+$, $K^+$, $Al^{3+}$, $Fe^{2+}$, $Fe^{3+}$, $Ca^{2+}$, $Mg^{2+}$, $NH_4^+$ and $Zn^{2+}$; $Q^{s-}$ is absent or a physiologically acceptable counter anion; and m−s=n, dissolved in a consumable solvent or solvents in a concentration up to about 40% by weight of the composition to provide a high concentration liquid low-calorie sweetener.

8. A liquid low-calorie sweetener according to claim 7, wherein the solvent is ethanol.

9. A liquid low-calorie sweetener according to claim 8, wherein $X^{m+}Q^{s-}$ is selected from the group consisting of $Mg(OH)^+$, $Al(OH)_2^+$ and $Ca(OH)^+$ and n is 1.

10. A liquid low-calorie sweetener according to claim 8, wherein $X^{m+}Q^{s-}$ is selected from the group consisting of $Fe_2O_2^{2+}$ and $Fe^{2+}$ and n is 2.

11. A liquid low-calorie sweetener according to claim 8, wherein $Q^{s-}$ is absent, n is 1 and $X^{m+}$ is selected from $Na^+$, $K^+$ and $NH_4^+$.

* * * * *

UNITED STATES PATENT AND TRADEMARK OFFICE
CERTIFICATE OF CORRECTION

PATENT NO.   : 6,291,004 B1
DATED        : September 18, 2001
INVENTOR(S)  : Indra Prakash et al.

Page 1 of 2

It is certified that error appears in the above-identified patent and that said Letters Patent is hereby corrected as shown below:

Column 2,
Lines 1-9,

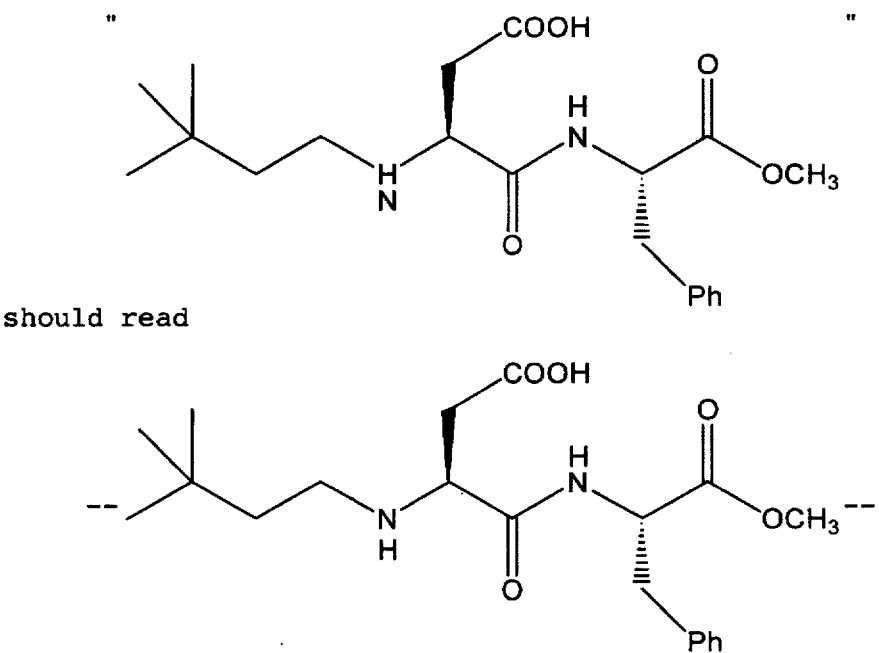

Column 4,
Line 17, "-1-L-α-" should read -- -L-α- --.

UNITED STATES PATENT AND TRADEMARK OFFICE
CERTIFICATE OF CORRECTION

PATENT NO. : 6,291,004 B1
DATED : September 18, 2001
INVENTOR(S) : Indra Prakash et al.

It is certified that error appears in the above-identified patent and that said Letters Patent is hereby corrected as shown below:

<u>Column 5,</u>
Line 1, "phenylalaninel-methyl" should read -- phenylalanine 1-methyl --.

Signed and Sealed this

Fifth Day of March, 2002

*Attest:*

*Attesting Officer*

JAMES E. ROGAN
*Director of the United States Patent and Trademark Office*